United States Patent
Cavagna et al.

(10) Patent No.: US 7,335,208 B2
(45) Date of Patent: Feb. 26, 2008

(54) TIGHTENING INSTRUMENT FOR ORTHOPAEDIC SURGERY OF THE SPINE

(75) Inventors: Remi Cavagna, Ploemeur (FR); Denis Huten, Vincennes (FR); Hugues Malandain, Southaven, TN (US)

(73) Assignee: Sofamor S.N.C., Roissy CDG Cedex (FR)

( * ) Notice: Subject to any disclaimer, the term of this patent is extended or adjusted under 35 U.S.C. 154(b) by 864 days.

(21) Appl. No.: 10/148,350

(22) PCT Filed: Dec. 1, 2000

(86) PCT No.: PCT/IB00/01786

§ 371 (c)(1),
(2), (4) Date: Oct. 9, 2002

(87) PCT Pub. No.: WO01/39930

PCT Pub. Date: Jun. 7, 2001

(65) Prior Publication Data

US 2003/0114860 A1    Jun. 19, 2003

(30) Foreign Application Priority Data

Dec. 3, 1999    (FR) .................................. 99 15288

(51) Int. Cl.
*A61B 17/58* (2006.01)

(52) U.S. Cl. ..................................... 606/104

(58) Field of Classification Search .............. 606/61, 606/72, 73, 104; 411/2, 5, 3, 386; 72/391; 81/467, 471, 57.37, 59.1, 442

See application file for complete search history.

(56) References Cited

U.S. PATENT DOCUMENTS

| 881,075 | A | * | 3/1908 | Hosking | 408/139 |
| 1,063,304 | A | * | 6/1913 | Titus, Jr. | 81/441 |
| 3,191,486 | A | * | 6/1965 | Gibbens | 411/4 |
| 3,753,625 | A | * | 8/1973 | Fabrizio et al. | 408/239 R |
| 4,838,264 | A | * | 6/1989 | Bremer et al. | 606/104 |
| 6,155,147 | A | * | 12/2000 | Dzieman | 81/473 |

FOREIGN PATENT DOCUMENTS

FR    2 486 852    1/1982

* cited by examiner

Primary Examiner—Anhtuan T. Nguyen
Assistant Examiner—Tuan V. Nguyen
(74) Attorney, Agent, or Firm—Woodard, Emhardt, Moriarty, McNett & Henry LLP

(57) ABSTRACT

The tightening instrument is made up of two parts (2,4) joined to each other by means which are designed to automatically uncouple the said two parts (2,4) by shearing rupture of a pin (8) when a predetermined tightening torque is reached, a first (2) of the two parts being provided with a means (3) permitting driving, characterized in that the second (4) of the two parts is a rod whose end (5) opposite its tightening end (6) is adapted to be introduced into a complementary recess (7) formed in the first part (2), and in that the said end (5) includes an axial reservoir (15) for receiving the broken end section (18) of the pin (8).

38 Claims, 3 Drawing Sheets

TIGHTENING INSTRUMENT FOR ORTHOPAEDIC SURGERY OF THE SPINE

The present invention relates to a tightening instrument intended especially, but not exclusively, to be used in orthopedic surgery, especially of the spine, for screwing threaded plugs or screws onto implants.

BACKGROUND OF THE INVENTION

French Patent Application FR-A-2,723,837 discloses automatically breaking implants made up of nuts which are divided into two sections separated is by a peripheral central zone which breaks at a predetermined tightening torque. For the small sizes of such automatically breaking implants, the end of the screwdriver engaged in the corresponding impression of the implant is of very small dimensions, its diameter being a few millimeters. On account of this small size of the end of the screwdriver, it can happen, as a result of insufficient mechanical strength when the breaking torque is reached, or even before it is reached, that this end breaks. It is then necessary to replace the screwdriver.

Moreover, when this automatically breaking nut has reached its breaking torque without the end of the screwdriver being broken, surgeons often tend to want to give an additional turn to the remaining part of the nut, screwed into the implant, and this after the nut has broken. This additional tightening is undesirable and can cause the end of the screwdriver to break because the torque exerted is greater than the breaking torque.

One solution to this problem is to provide a tightening instrument which is designed such that it can no longer be used once the defined breaking torque has been reached.

Document U.S. Pat. No. 4,838,264 proposes instruments of this type intended for surgical applications. In a first illustrative embodiment, a cap provided with a grip is engaged on the head of a screw. It includes a zone of less resistance which breaks under torsion once the torque applied by the cap exceeds a given value. The cap is therefore used only once. In a second illustrative embodiment, the tightening instrument is made up of two parts which are connected via a solid element of polygonal cross section provided with a zone of less resistance which breaks under torsion when the torque applied exceeds a given value. This solid component can therefore be used only once. For surgical applications, this instrument has the disadvantage that it cannot be immediately reused since the component which can break off has to be replaced. Moreover, the two instruments which have just been described comprise disposable rupturing components which are relatively voluminous and are expensive to produce.

In general mechanics, instruments area known in which the torque-limiting function is ensured by a pin which connects two elements of the instrument and which breaks by shearing once a predetermined applied torque value is reached. In this regard, mention may be made of documents U.S. Pat. Nos. 4,703,677 and 3,753,625. In these, the rupturing component is of small dimensions and thus not expensive. However, the known configurations using a pin are not applicable without difficulty to surgery. In particular, there is nothing to retain the pieces of the broken pin, and these pieces risk falling into the operating site when the instrument is used.

SUMMARY OF THE INVENTION

The object of the invention is to propose a tightening instrument with applied torque limitation which can be employed completely safely for surgical applications and is inexpensive to use.

To this end, the subject of the invention is a tightening instrument made up to two parts joined to each other by means which are designed to automatically uncoupled the said two parts by shearing rupture of a pin when a predetermined tightening torque is reached, a first of the two parts being provided with a means permitting driving, characterized in that the second of the two parts is a rod whose upper end opposite its tightening end is adapted to be introduced into a complementary recess formed in the first part, and in that the said upper end includes an axial reservoir for receiving the broken end section of the pin.

In a first alternative embodiment of the invention, the said pin is engaged transversely through an opening formed in the wall of the said recess and through the upper end of the rod introduced into the recess.

The instrument preferably comprises means for guiding and holding the pin in the said opening. They can consist of a tubular section integral with the said element and coaxial to the opening for introduction of the pin.

The said tubular section can comprise a retainer screw passing through its side wall and able to abut against the pin.

In a second alternative embodiment of the invention, the said pin is engaged longitudinally through a channel formed in the first part, substantially parallel to the longitudinal axis of the instrument and offset laterally relative to it, and through a seat formed on the upper face of the upper end of the rod at the edge of the said axial reservoir.

The instrument can comprise a plurality of seats formed on the upper face of the upper end of the rod.

It can comprise means for indicating to the user if the channel and a seat are placed in the continuation of each other, such as a sleeve inserted in the bottom of the recess and having a ball moving freely inside the sleeve and able to protrude inside the recess in order to penetrate into one of the seats.

The lower part of the channel can be formed through a component made of a material which has a greater resistance to the stresses exerted on it by the pin than the material constituting the remainder of the first part.

The instrument can comprise means for closing off the upper end of the channel.

The said closure means are preferably made integral with the said first part. They can consist of a pusher inserted into the first part substantially perpendicular to the longitudinal axis of the instrument and comprising an orifice which can be brought by the user into the continuation of the channel, and a spring maintaining the pusher at rest in a position in which the channel and the orifice of the pusher are not in the continuation of each other.

The invention also concerns the use of such an instrument in orthopedic surgery, especially of the spine, as a screwdriver for screwing threaded plugs or screws onto implants.

As will be appreciated, the invention consists in joining the two parts of the tightening instrument by means of a pin which can break by shearing, and in providing means for retaining the broken end of the pin inside the instrument itself. This pin can be arranged transversely relative to the longitudinal axis of the instrument, or parallel to this axis and axially offset thereto. Preferably, means for retaining the intact part of the pin are also provided. If the pin is of sufficient length, it can be easily and rapidly reused after it has been pushed back manually inside the instrument or after it has itself resumed its position simply by gravity.

Such an instrument used as a screwdriver is particularly, advantageous in the field of orthopedic surgery, especially of the spine, for screwing threaded plugs or screws onto implants.

However, it is evident that this instrument is open to a great many other applications in fields other than orthopedic surgery, for example for automated assembly of parts avoiding crushing of sealing joints, etc.

The invention will now be described with reference to the attached drawings which illustrate several embodiments thereof by way of nonlimiting examples.

DETAILED DESCRIPTION OF THE PREFERRED EMBODIMENTS

Figure 1:
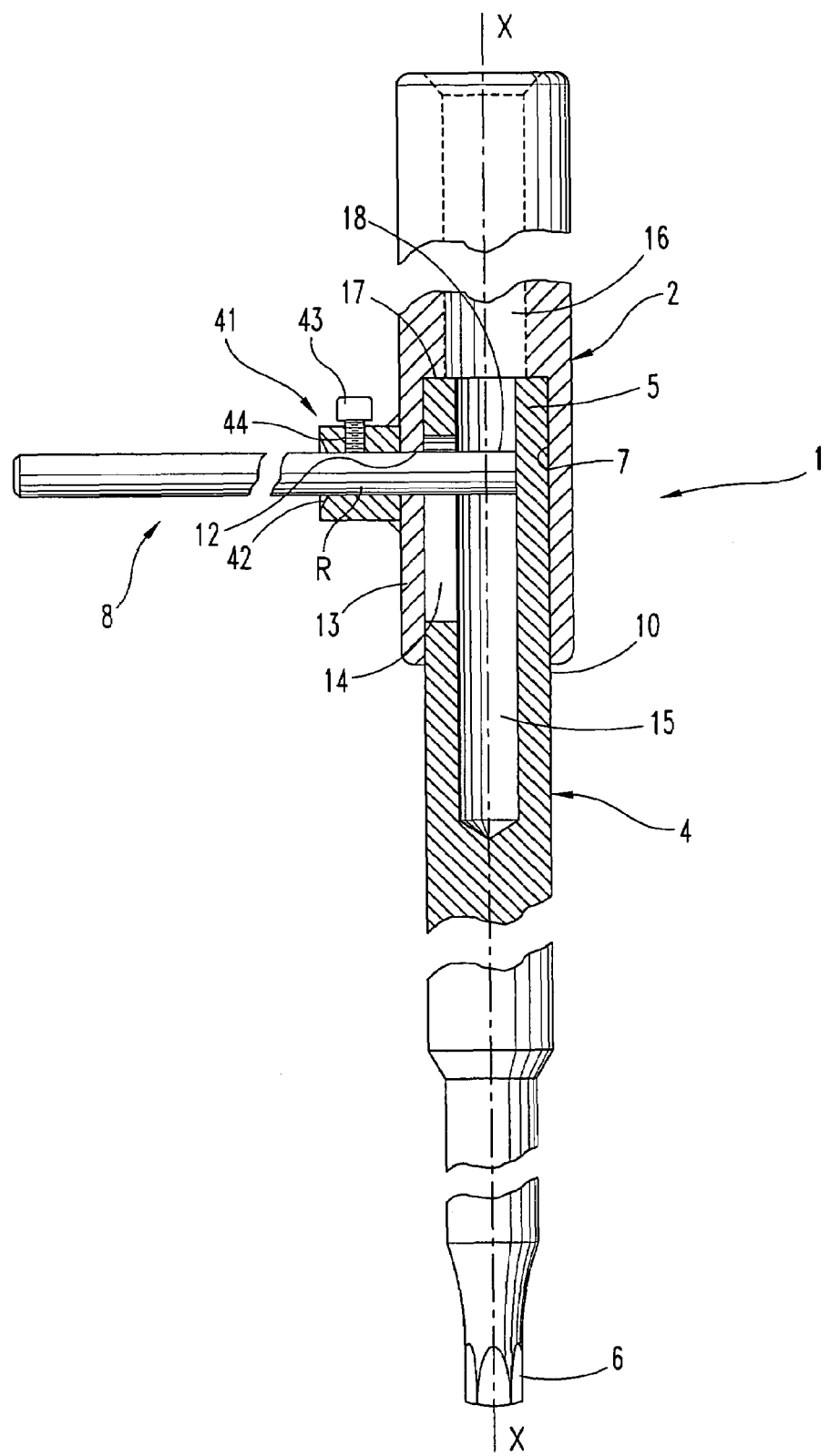
FIG. 1 is a view, half in longitudinal section and half in elevation, of a first embodiment of the tightening instrument according to the invention, equipped with a transverse pin.
Figure 2:
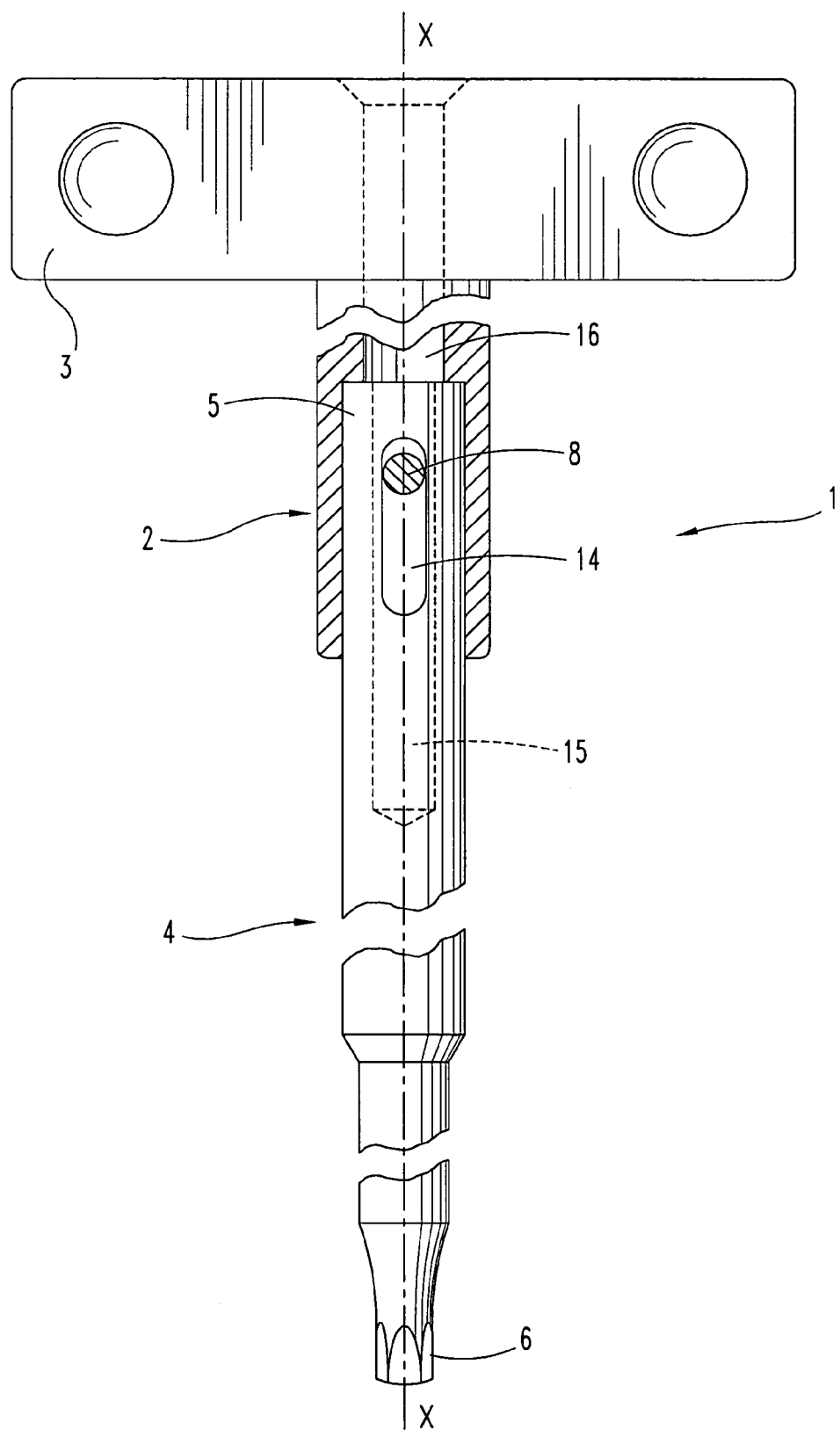
FIG. 2 is a view similar to FIG. 1 in a plane perpendicular to that of FIG. 1, showing the whole of the instrument

The tightening instrument represented in FIGS. 1 and 2 is open to many applications in various fields, in particular as a screwdriver in orthopedic surgery of the spine, for example for screwing nuts or screws.

This instrument 1 comprises two parts, namely a first part made up of an element or body 2, which is tubular in this embodiment and which is equipped with a means of driving, for example a manual grip 3, preferably attached to the proximal end of body 2; the instrument 1 also comprises a second part or body 4 made up of a rod whose proximal end 5, opposite its distal profiled tightening end 6, is adapted to be able to be introduced into a complementary recess 7 of the tubular element 2. In other words, element 2 is contacted to part 4 by mutually engageable male contact 5 and female contact 7. The recess 7 is continued by an axial channel 16 which is coaxial with the longitudinal axis XX of the instrument 1 and which opens to the outside at the level of its grip 3. The recess 7 is separated from the channel 16 by an annular shoulder 17 forming a stop at the distal end of body 2 for the end 5 of the rod 4 to meet.

The joining means between the two parts 2 and 4 comprise a pin 8 which can be engaged transversely through an opening 12 formed in the wall 13 of the recess 7 and through the end 5 of the rod 4. For this purpose, the wall of the end 5 is pierced with a slot 14 for passage of the pin 8. As is represented, the slot 14 can be oblong in a direction parallel to the longitudinal axis XX of the instrument 1, and it opening into an axial reservoir 15 formed in the end 5 of the rod 4. This reservoir 15 constitutes a blind hole in the rod 4.

When the two parts 2, 4 are engaged, part of the slot 14 is situated opposite the opening 12, which makes it possible to introduce the pin 8 into the opening 12, into the slot 14 and into the reservoir 15 until the end section of pin 8 is stopped by the wall of the latter.

The tubular element 2 can be telescopically moved within rod 4 along the longitudinal axis XX and free in rotation about this same axis if the pin 8 is withdrawn.

Means are provided for guiding and holding the pin 8 in the opening 18. In the embodiment shown, these means consist of a tubular section or body 41 integral with the element 2 and extending coaxial to the opening 12. The opening of this tubular section 41 preferably has a bevel 42 making it easier to introduce the pin 8. The tubular section 41 can also be associated with a means for blocking the pin 8, for example a retaining screw 43 inserted in a tapped hole 44 formed in the side wall of the tubular section 41. This screw is intended to abut against the pin 8 after it has been put in place. The pressure exerted by the screw 43 on the pin 8 prevents the latter from leaving its seat under the effect of weight when the instrument (which is normally used in a vertical position in its applications in orthopedic surgery) is placed in an inclined position during, its maneuvers or transport The instrument 1 which has just been described functions the following way.

First, the rod 4 is introduced into the tubular element 2 by inserting its end 5 into the recess 7 until it comes into abutment on the shoulder 17. The pin 8 is then introduced into the tubular section 41 for guiding into the opening 12, into the slot 14 and into the axial reservoir 15. The instrument 1 is then ready for use, in particular as a screwdriver if it is equipped with a profiled point 6. The pin 8 is chosen with a diameter and a material such that it can be broken by shearing at the level R of the junction between the parts 2 and 4 at a predetermined breaking torque.

Thus, when this torque is reached, the pin 8 breaks at this location R, and the broken end section 18 falls to the bottom of the reservoir 15, whilst the rest of the pin 8 is preferably held in place by the screw 43. Consequently, the two parts 2 and 4 of the instrument 1 become completely uncoupled, and this automatically, so that the user can no longer exert any supplementary tightening. On the other hand, the different parts of the pin 8 are maintained integral with the instrument 1 or inside the reservoir 15; they do not risk falling outside the instrument 1, which is important with regard to the application of the instrument 1 in surgery, where it is necessary to avoid the risk of a piece of the pin 8 falling into the operating site.

To use it again, it is necessary to loosen the screw 43 and to once more engage the same pin 8 or a new pin 8 through the opening 12, the slot 14 and the reservoir 15 until its end comes into abutment against the wall of the latter. The screw 43 is then tightened again, and instrument 1 can then be used again, until a further breaking of the pin 8.

The length of the pin 8 is advantageously determined so as to permit at least two successive breaks of the same pin 8, the broken sections being collected in the reservoir 15. Thus, as seen in one embodiment in FIG. 1, pin 8 may have a length greater than twice the width of reservoir 15. The latter can be easily emptied of these sections by way of the evacuation channel 16 formed in the element 2, or else by separating the two parts 2 and 4. For use of the instrument in a surgical field, it is preferable to provide removable means of closing off the evacuation channel 16 in order to ensure that the broken sections of the pin 8 are kept inside the instrument 1 as long as the instrument is in use near the body of the patient.

It is possible to complete the instrument 1 by providing a series of connecting pins 8, made of the same material but with different diameters, and each therefore having a defined breaking torque. Similarly, it is also possible to use a series of pins 8 of the same diameter, but made of different materials, with different resistance to shearing, so that each type of pin 8 corresponds to a defined breaking torque. The instrument 1 and its pin or pins 8 can be made of any of the materials normally used for the manufacture of surgical instruments or implants, in particular stainless steel, titanium, etc.

Figure 3:
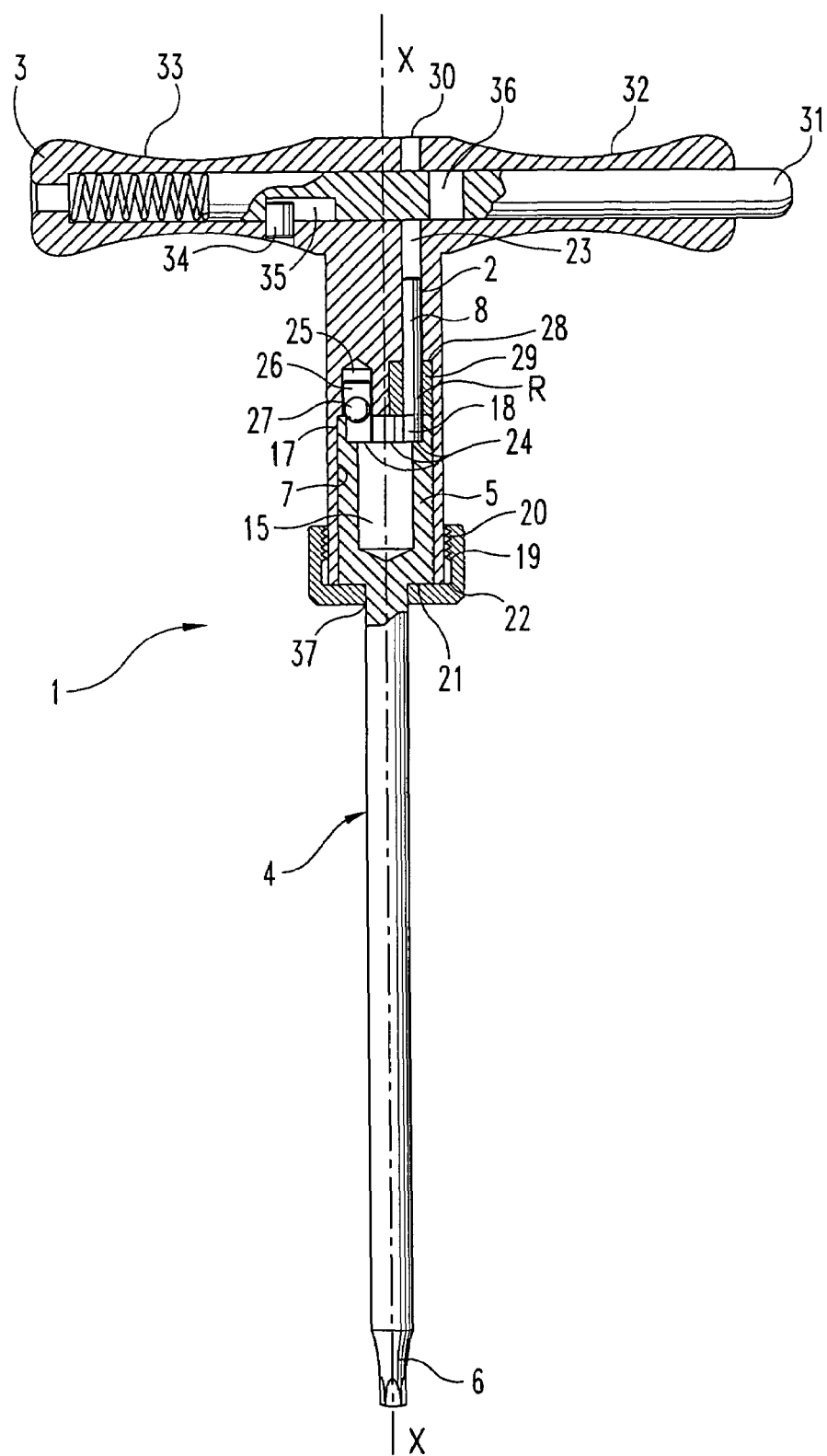
FIG. 3 is a longitudinal section through a second embodiment of the instrument according to the,invention, equipped with a longitudinal pin.

In the alternative embodiment of the invention represented in FIG. 3, those elements in common with the alternative embodiment represented in FIGS. 1 and 2 are designated by the same reference labels.

Here, the instrument is again designed with a first part 2 provided with a drive means such as a grip handle 3, and a second part 4 of which one end 6 is profiled in such a way as to be able to drive a component which is to be tightening, and of which the other end 5 is intended to be inserted in a recess 7 formed in the first part 2. The two parts 2, 4 are joined by means of an internally threaded ring 19 cooperating on the one hand with a threading 20 formed on the outer wall of the first part 2 and on the other hand with a shoulder 21 formed on the second part 4 and intended to rest on the bottom 22 of the internal space of the ring 19 which is itself provided with an orifice 37 permitting the passage of the rod of the second part 4. After it has been tightened, the ring 19 holds the two parts 2, 4 of the instrument 1 together while at the same time permitting their relative rotation about the longitudinal axis XX of the instrument 1.

The complete interconnection of the two parts 2, 4, by which the instrument 1 is rendered operative, is once again ensured by a pin 8 which can break by shearing. In contrast to the previous example, this pin 8 is here inserted parallel to the longitudinal axis XX of the instrument 1. For this purpose, a channel 23 is formed through the first part 2, parallel to the axis XX, and laterally offset relative thereto. As it passes right through the first part 2, the channel 23 emerges outside the instrument 1 and inside the recess 7.

The pin 8 is inserted in the channel 23 from the outside, after the two parts 2, 4 of the instrument 1 have been joined together by means of the ring 19. Its lower end thus takes up a position in a seat 24, the depth of which is, for example, of several mm, formed on the upper face of the end 5 of the second part 4 inserted in the recess 7. This seat 24 is situated at the edge of the axial reservoir 15. As in the previous example, the pin 8 is designed to break by shearing at the level R of the junction between the two parts 2, 4 of the instrument 1 once the tightening torque applied to the instrument and transmitted to the element to be tightened reaches a predetermined value which is not to be exceeded. After rupture, the broken lower end of the pin 8 falls to the bottom of the axial reservoir 15. It then suffices for the user to bring the channel 23 and the seat 24 back into line with each other, by rotating the grip 3, so that the reset of the pin 8 is reinserted in the seat 24 by gravity, thus rendering the instrument 1 once again ready for use. The length of the pin 8 is optimally calculated to authorize a number of successive tightenings which is sufficient to ensure that only a minimum number of replacements of the pin 8 need be made during a series of uses of the instrument 1.

Compared with the configuration described earlier and shown in FIGS. 1 and 2, this configuration with longitudinal pin 8 has the particular advantage of reducing the lateral size of the device since the pin 8 does not extend outside the instrument. Moreover, the rearming of the instrument 1 after rupturing of the pin 8 is effected rapidly by a simple relative rotation of the two parts 2, 4 of the instrument 1 which is held substantially vertical, the pin 8 resuming its position in its seat 24 simply by gravity.

The instrument 1 in this alternative embodiment of the Invention advantageously includes one or more of the following characteristics.

As is shown, several seats 24 for the pin 8 can be formed on the upper face of the end 5 of the second part 4 (for example two seats 24 offset at 180° or four seats 24 offset at 90°). Rearming of the instrument 1 is thereby facilitated since this reduces the extent of the grip 3 in order to restore the alignment between the channel 23 and any given seat 24.

When several seats 24 are capable of receiving the pin 8, as is shown, a seat 25 can be formed in the bottom of the recess 7 of the first element 2. A sleeve 26 is placed in this seat 25 and is provided at its end with a ball 27 which moves freely inside the sleeve 26 and is able to protrude slightly into the recess 7. The position of this seat 25 enclosing the sleeve 26 is such that when the ball 27 is above one of the seats 24 capable of receiving the pin 8 and is inserted in this seat 24, the channel 23 is situated opposite another seat 24 which can receive the pin 8. In this way, prior to the insertion of the pin 8, the user can obtain the alignment between the channel 23 and a seat 24 without having to do so by trial and error once he feels a slight resistance to rotation of the grip 3, he knows that the ball 27 has penetrated into a seat 24 and that the alignment sought has been obtained.

The lower part of the channel 23 is preferably formed in a component 28 which is itself inserted in a seat 29 formed in the bottom of the recess 7. This component 28 is made of a material having mechanical properties (especially great hardness) which render it particularly resistant to the stresses exerted on it by the pin 8 during shearing thereof. This avoids rapid deterioration of that portion of the first part 2 of the instrument 1 which ensures the shearing of the pin 8. The rupture of the pin 8 is therefore always clean and reproducible under conditions of identical stressing from one use to the next. The component 28 can be made, for example, of a steel which has undergone thermal treatment and/or surface treatment giving it the desired properties. Using the component 28 means that the whole of the first part 2 of the instrument 1 does not have to be made of such a resistant or specially treated material, which would be very expensive. The component 28 can also be replaced whenever necessary in order to maintain the performance of the instrument 1 instead of having to replace the first part 2 in its entirety.

It is preferably to provide means for dosing off the orifice 30 of the channel 23 in order to prevent the pin 8 from escaping from the channel 23 during manipulation of the instrument 1. A simple plug can suffice for this purpose, but it is also possible to use, for example, a device which is operably included with the first part 2 of the instrument 1, such as that shown in FIG. 3. This device comprises a pusher 31 inserted in an orifice 32 of corresponding shape formed in the grip 3 and with an orientation substantially perpendicular to the axis XX. A spring 33 inserted at the bottom of the orifice 32 seeks to expel the pusher 31, but this expulsion is prevented by a stop 34 fixed in the grip 3 and cooperating with a notch 35 formed in the pusher 31. An orifice 36 oriented parallel to the axis XX passes through the pusher 31 in such a way as to be able to be placed in the continuation of the channel 23 enclosing the pin 8. When the user wishes to place a new pin 8 in the instrument 1, he pushes the pusher 31 back by compressing the spring 33, in such a way as to place the orifice 36 of the pusher 31 in the continuation of the channel 23, he introduces the pin 8 into the channel 23 via the orifice 30, then releases the pusher 31. The channel 23 is thereby closed off by the pusher 31, and the pin 8 cannot escape from the instrument 1.

Where the instrument which has just been described is used in orthopedic surgery, in particular of the spine, the invention affords a number of advantages:

1. The use of an automatically breaking nut, such as that described in the aforementioned French patent, becomes redundant, since the break no longer occurs on the implant itself, but inside the screwing instrument. It is thus possible to use conventional implants which are simpler and whose manufacturing cost is significantly lower.

2. Because the break occurs inside the instrument, uncoupling these two parts, it becomes impossible for the surgeon to tighten the implant with a torque greater than the breaking torque, which avoids any unwanted additional tightening.

3. The risk of breaking of the screwing end of the instrument, for screws and nuts of very small dimensions, is eliminated, as has already been stated.

4. The omission of the breaking extensions on the automatically breaking nuts such as those described by the aforementioned patent has the advantage of considerably reducing the risk of conflict, that is to say of contact, between heads of nuts in spines with a high degree of lordosis. This is because a high degree of lordosis causes a marked relative inclination between the bone anchoring members of the vertebras in question, which can place in contact the heads of the nuts which lock these anchoring members, which constitutes an obvious impediment for the surgeon.

It is of course possible to imagine alternatives to the examples shown without departing from the spirit of the invention. Thus, means for driving the first part 2 of the instrument 1 can consist of something other than a grip and can permit said driving with the aid of a separate instrument. Likewise, in the second example described, it is possible to imagine means other than the sleeve 26 for locating the correct angular position of the first part 2, prior to insertion of the pin 8, and other means for dosing off the channel 23.

The instrument according to the invention can be used in orthopedic surgery, especially of the spine, as a screwdriver for screwing threaded plugs or screws onto implants. The invention eliminates the risk of the screwing end of the instrument breaking as a result of insufficient mechanical strength when this end has very small dimensions, and it prevents any unwanted supplementary screwing beyond the breaking torque. This increases the reliability of the device implanted in the body of the patient, which limits the risk of having to reoperate on the patient following failure of this device, which would be caused by excessive or insufficient tightening of one of its elements.

What is claimed is:

1. An instrument for tightening bone screws into a patient during orthopedic surgery, comprising: a first body and a second body, said first and second bodies sharing a common axis of rotation; said fast body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein said first and second bodies have a longitudinal side; wherein said second body has a second passage that opens between the reservoir and the longitudinal side of said second body; wherein said first body has a first passage that opens between the second passage in said second body and the longitudinal side of said first body; and wherein said shear pin is inserted through the first and second passages; and further including a third body that is fixedly secured on the longitudinal side of said first or second body; said third body having a third passage therethrough that opens into said first and second passages; and wherein said shear pin is received inside the third passage.

2. The instrument of claim 1, including means for guiding and holding said shear pin within at least one of said passages.

3. The instrument of claim 1, further including a setscrew threadably engageable against said shear pin.

4. An instrument for tightening bone screws into a patient during orthopedic surgery, comprising: a first body and a second body, said first and second bodies sharing a common axis of rotation; said first body having a distal end; said second body having a reservoir therein, said second body having, a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, and wherein the reservoir of said second body includes a plurality of seats to accept the end section of said shear pin, and wherein said first body has a channel that opens to the distal end of said first body and a proximal end, and the channel in the first body is open between the proximal and distal ends of the said first body.

5. The instrument of claim 4 wherein said first body has a channel that opens to the distal end of said first body, said instrument including means for indicating to the user that said channel and seat are coaxially aligned.

6. The instrument according to claim 4 Wherein said first body has a channel that opens to the distal end of said first body, and wherein the channel in said first body is formed through a component made of a material that is harder than the material from which said shear pin is made.

7. The instrument of claim 4 wherein said first body has a channel that opens to the distal end of said first body and a proximal end, and including means for closing the channel near the proximal end of said first body.

8. The instrument of claim 4, wherein said reservoir has an axial dimension, and said end section of said shear pin is smaller than said axial dimension of said reservoir, whereby said end section drops into said reservoir after said shear pin breaks.

9. The instrument of claim 4, wherein said shear pin is not coaxial with said common axis of rotation.

10. The instrument of claim 4, wherein after said shear pin breaks, a new end section of said shear pin is created, and said reservoir has a volume sufficient to hold a plurality of end sections of said shear pin.

11. The instrument of claim 4, wherein said first body has a channel that opens to the distal end of said first body, wherein the reservoir of said second body communicates with said channel; and wherein said shear pin is received with the channel of said first body and the seat in the reservoir of said second body.

12. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, and wherein the reservoir of said second body includes a plurality of seats to accept the end section of said shear pin, and wherein said first body has a channel that opens to the distal end of said first body, said instrument including a member inserted in the first body substantially perpendicular to the longitudinal axis of the of the shear pin; said member having an orifice therein which can be brought by the user into the channel, said instrument further including a spring maintaining the member in a normally closed position in which the channel and the orifice of the member are not in the continuation of each other.

13. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein said reservoir has a width dimension and said shear pin has a length greater than twice said width dimension, so that after said shear pin is broken and said end section is within said reservoir, a new end section of said shear pin is positioned in said reservoir so that said new end section can be broken from said shear pin.

14. The instrument of claim 13, wherein said first and second bodies have a longitudinal side; wherein said second body has a second passage that opens between the reservoir and the longitudinal side of said second body; wherein said first body has a first passage that opens between the second passage in said second body and the longitudinal side of said first body; and wherein said shear pin is inserted through the first and second passages.

15. The instrument of claim 14, including means for guiding and holding said shear pin within at least one of said passages.

16. The instrument of claim 13, wherein the reservoir of said second body includes a plurality of seats to accept the end section of said shear pin.

17. The instrument of claim 16, including means for indicating to the user that said channel and seat are coaxially aligned.

18. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein after said shear pin breaks, a new end section of said shear pin is created and is positioned in said reservoir so that said new end section can be broken from said shear pin, and said reservoir has a volume sufficient to hold a plurality of end sections of said shear pin.

19. The instrument of claim 18, wherein said first and second bodies have a longitudinal side; wherein said second body has a second passage that opens between the reservoir and the longitudinal side of said second body; wherein said first body has a first passage that opens between the second passage in said second body and the longitudinal side of said first body; and wherein said shear pin is inserted through the first and second passages.

20. The instrument of claim 19, including means for guiding and holding said shear pin within at least one of said passages.

21. The instrument of claim 18, wherein the reservoir of said second body includes a plurality of seats to accept the end section of said shear pin.

22. The instrument of claim 21, wherein said first body has a channel that opens to the distal end of said first body, said instrument including means for indicating to the user that said channel and seat are coaxially aligned.

23. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein said first and second bodies have a longitudinal side; wherein said second body has a second passage that opens between the reservoir and the longitudinal side of said second body; wherein said first body has a first passage that opens between the second passage in said second body and the longitudinal side of said first body; and wherein said shear pin is inserted through the first and second passages; and wherein said reservoir has a width dimension and said shear pin has a length greater than twice said width dimension, so that after said shear pin is broken and said end section is within said reservoir, a new end section of said shear pin can be positioned in said reservoir.

24. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein said first and second bodies have a longitudinal side; wherein said second body has a second passage that opens between the reservoir and the longitudinal side of said second body; wherein said first body has a first passage that opens between the second passage in said second body and the longitudinal side of said first body; and wherein said shear pin is inserted through the first and second passages, and wherein after said shear pin breaks, a new end section of said shear pin is created, and said reservoir has a volume sufficient to hold a plurality of end sections of said shear pin.

25. The instrument of claim 24, wherein said shear pin has a length such that when said end section is in said reservoir, an opposite portion of said shear pin is outside of said first body and said second body.

26. The instrument of claim 24, wherein said reservoir has an axial dimension, and said end section of said shear pin is smaller than said axial dimension of said reservoir, whereby said end section drops into said reservoir after said shear pin breaks.

27. The instrument of claim 24, wherein said shear pin is not coaxial with said common axis of rotation.

28. The instrument of claim 24, wherein said shear pin is parallel to and offset from said common axis of rotation.

29. The instrument of claim a 24, wherein said shear pin is oriented substantially perpendicular to said common axis of rotation.

30. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, and wherein the reservoir of said second body includes a plurality of seats to accept the end section of said sheer pin, and wherein said shear pin is parallel to and offset front said common axis of rotation.

31. The instrument of claim 30, including means for indicating to the user that said channel and seat are coaxially aligned.

32. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, and wherein the reservoir of said second body includes a plurality of seats to accept the end section of said shear pin, wherein said reservoir has a width dimension and said shear pin has a length greater than twice said width dimension, so that after said shear pin is broken and said end section is within said reservoir, a new end section of said shear pin can be positioned in said reservoir.

33. The instrument of claim 32, including means for indicating to the user that said channel and seat are coaxially aligned.

34. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with, said end section positioned at least partially in the reservoir of said second body, whereby the reservoir can receive said end section when said shear pin breaks, wherein said reservoir has an axial dimension, and said end section of said shear pin is smaller than said axial dimension of said reservoir, whereby said end section drops into said reservoir after said shear pin breaks; and wherein said first and second bodies have a longitudinal side, said first body has a first passage and said second body has a second passage, said shear pin being inserted through the first and second passages; and further including a third body that is fixedly secured on the longitudinal side of said first or second body; said third body having a third passage therethrough that opens into said first and second passages; and wherein said shear pin is received inside the third passage.

35. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein said shear pin is not coaxial with said common axis of rotation; and wherein said first and second bodies have a longitudinal side, said first body has a first passage and said second body has a second passage, said shear pin being inserted through the first and second passages; and further including a third body that is fixedly secured on the longitudinal side of said first or second body; said third body having a third passage therethrough that opens into said first and second passages; and wherein said shear pin is received inside the third passage.

36. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein said reservoir has a width dimension and said shear pin has a length greater than twice said width dimension, so that after said shear pin is broken and said end section is within said reservoir, a new end section of said shear pin can be positioned in said reservoir; and wherein said first and second bodies have a longitudinal side, said first body has a first passage and said second body has a second passage, said shear pin being inserted through the first and second passages; and further including a third body that is fixedly secured on the longitudinal side of said first or second body; said third body having a third passage therethrough that opens into said first and second passages; and wherein said shear pin is received inside the third passage.

37. An instrument for tightening bone screws into a patient during orthopedic surgery, comprising: a first body and a second body, said first and second bodies sharing a common axis of rotation; said first body having a distal end; said second body having a reservoir therein, said second body having a distal end having a profile to engage a bone screw; and a shear pin with an end section, said shear pin being inserted through said first and second bodies with said end section positioned at least partially in the reservoir of said second body, whereby the reservoir can receive said end section when said shear pin breaks, wherein after said shear pin breaks, a new end section of said shear pin is created, and said reservoir has a volume sufficient to hold a plurality of end sections of said shear pin; and wherein said first and second bodies have a longitudinal side, said first body has a first passage and said second body has a second passage, said shear pin being inserted through the first and second passages; and further including a third body that is fixedly secured on the longitudinal side of said first or second body; said third body having a third passage therethrough that opens into said first and second passages; and wherein said shear pin is received inside the third passage.

38. The instrument of claim 24, including means for guiding and holding said shear pin within at least one of said passages.

* * * * *